United States Patent
Wang et al.

(10) Patent No.: US 10,386,316 B2
(45) Date of Patent: Aug. 20, 2019

(54) DEVICE FOR IN-SITU MEASURING ELECTRICAL PROPERTIES OF CARBON NANOTUBE ARRAY

(71) Applicants: Tsinghua University, Beijing (CN); HON HAI PRECISION INDUSTRY CO., LTD., New Taipei (TW)

(72) Inventors: Jiang-Tao Wang, Beijing (CN); Xiang Jin, Beijing (CN); Peng Liu, Beijing (CN); Yang Wei, Beijing (CN); Kai-Li Jiang, Beijing (CN); Shou-Shan Fan, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 322 days.

(21) Appl. No.: 15/598,205

(22) Filed: May 17, 2017

(65) Prior Publication Data
US 2017/0336338 A1  Nov. 23, 2017

(30) Foreign Application Priority Data
May 20, 2016 (CN) .......................... 2016 1 0336949

(51) Int. Cl.
*H01L 51/00* (2006.01)
*G01N 27/02* (2006.01)
(Continued)

(52) U.S. Cl.
CPC ........... *G01N 27/02* (2013.01); *C01B 32/158* (2017.08); *C23C 16/26* (2013.01); *C23C 16/46* (2013.01);
(Continued)

(58) Field of Classification Search
CPC . H01L 51/0048; H01L 22/14; H01L 51/0002; H01L 51/0031; G01N 27/02;
(Continued)

(56) References Cited

U.S. PATENT DOCUMENTS 8,501,529 B2 * 8/2013 Yoon ..................... B82Y 10/00
257/40
10,011,488 B2 7/2018 Jiang et al.
(Continued)

FOREIGN PATENT DOCUMENTS

CN 101279372 10/2008
CN 101352669 1/2009
(Continued)

OTHER PUBLICATIONS

John Paul Pineda, et al., Electrical Conductivity Measurement of Carbon Nanotubes Film using Conductive Probe Atomic Force Microscopy (CP-AFM), Park Atomic Force (Year: 2019).*
(Continued)

*Primary Examiner* — Tung X Nguyen
*Assistant Examiner* — Robert P Alejnikov, Jr.
(74) *Attorney, Agent, or Firm* — ScienBiziP, P.C.

(57) ABSTRACT

A device for in-situ measuring electrical properties of a carbon nanotube array comprises a chamber, a substrate, a first electrode, a connecting wire, a second electrode, a support structure, and a measuring meter. The substrate, the first electrode, the connecting wire, the second electrode, and the support structure are located inside of the chamber. The measuring meter is located outside of the chamber, and the measuring meter is electrically connected to the first electrode and the second electrode. The first electrode defines a cavity, and the substrate is suspended in the cavity by interaction of the support structure, the second electrode, and the connecting wire.

16 Claims, 17 Drawing Sheets

(51) Int. Cl.
| | |
|---|---|
| H01L 21/66 | (2006.01) |
| C23C 16/26 | (2006.01) |
| C23C 16/46 | (2006.01) |
| G01N 27/22 | (2006.01) |
| G01R 15/12 | (2006.01) |
| G01R 29/24 | (2006.01) |
| G01R 31/02 | (2006.01) |
| C23C 16/52 | (2006.01) |
| G01N 27/04 | (2006.01) |
| C01B 32/158 | (2017.01) |
| B82Y 40/00 | (2011.01) |

(52) U.S. Cl.
CPC .......... *C23C 16/52* (2013.01); *G01N 27/041* (2013.01); *G01N 27/226* (2013.01); *G01R 15/12* (2013.01); *G01R 29/24* (2013.01); *G01R 31/025* (2013.01); *G01R 31/026* (2013.01); *H01L 22/14* (2013.01); *H01L 51/0002* (2013.01); *H01L 51/0031* (2013.01); *H01L 51/0048* (2013.01); *B82Y 40/00* (2013.01); *C01B 2202/22* (2013.01)

(58) Field of Classification Search
CPC .... G01R 1/04; G01R 1/0491; G01R 1/06744; G01R 1/073; G01R 1/07342; G01R 31/2601; G01R 31/2887; G01R 31/2891; G01R 1/0408; G01R 1/0433; G01R 1/0483; G01R 1/07314; G01R 31/26; G01R 31/2808; G01R 31/2886; G01R 1/07307
USPC .................. 324/649, 754.01, 754.08, 756.01
See application file for complete search history.

(56) References Cited

U.S. PATENT DOCUMENTS

| | | |
|---|---|---|
| 2002/0123230 A1 | 9/2002 | Hubacek |
| 2007/0059370 A1 | 3/2007 | Chou et al. |
| 2007/0134866 A1* | 6/2007 | Huang .................. B82Y 10/00 438/199 |
| 2007/0281086 A1 | 12/2007 | Hsiao |
| 2010/0284002 A1* | 11/2010 | Li .......................... G01N 25/18 356/301 |
| 2016/0023903 A1 | 1/2016 | Jiang et al. |
| 2016/0023908 A1 | 1/2016 | Jiang et al. |

FOREIGN PATENT DOCUMENTS

| | | |
|---|---|---|
| CN | 102329527 | 1/2012 |
| CN | 102936010 | 2/2013 |
| CN | 104692357 | 6/2015 |
| CN | 105439114 | 3/2016 |
| TW | 200711722 | 4/2007 |
| TW | I372188 | 9/2012 |
| TW | I386511 | 2/2013 |
| TW | 201604129 | 2/2016 |
| TW | 201604130 | 2/2016 |

OTHER PUBLICATIONS

Nicolo Chiodarelli, et al., Measuring the electrical resistivity and contact resistance of vertical carbon nanotube bundles for application as interconnects, 22 Nanotechnology 085302 (2011) (Year: 2011).*

Agnieszka Lekawa-Raus, et al., Electrical Properties of Carbon Nanotube Based Fibers and Their Future Use in Electrical Wiring, 24 Adv. Funct. Mater. 3661 (2014) (Year: 2014).*

Plasma-induced alignment of carbon nanotubes; Bower et al.; Applied Physics Letters; vol. 77, No. 9; p. 830-832; Aug. 7, 2000.

Spatially Selective Guided Growth of High-Coverage Arrays and Random Networks of Single-Walled Carbon Nanotubes and their Integration into Electronic Devices; Kocabas et al.; J. Am. Chem. Soc. 2006, 128, 4540-4541; Mar. 22, 2006.

Fabrication of Ultralong and Electrically Uniform Single-Walled Carbon Nanotubes on Clean Substrates; Wang et al.; Nano Letters 2009, vol. 9,No. 9; 3137-3141; Aug. 3, 2009.

* cited by examiner

US 10,386,316 B2

DEVICE FOR IN-SITU MEASURING ELECTRICAL PROPERTIES OF CARBON NANOTUBE ARRAY

CROSS-REFERENCE TO RELATED APPLICATIONS

This application claims all benefits accruing under 35 U.S.C. §119 from China Patent Application No. 201610336949.8, filed on May 20, 2016, in the China Intellectual Property Office, the disclosure of which is incorporated herein by reference.

FIELD

The present application relates to a device for in-situ measuring electrical properties of carbon nanotube array and a method for in-situ measuring electrical properties of carbon nanotube array.

BACKGROUND

Carbon nanotubes can be composed of a number of coaxial cylinders of graphite sheets, and have recently attracted a great deal of attention for use in different applications such as field emitters, gas storage and separation, chemical sensors, and high strength composites. At present, it is necessary to first take the carbon nanotubes out of the reaction chamber, and then measure the electrical properties of the carbon nanotubes. When the carbon nanotubes are taken out of the reaction chamber, the most intrinsic or primitive electrical properties of the carbon nanotubes will be changed by environmental changes. Accordingly, the measured electrical properties of the carbon nanotubes will be inaccurate.

What is needed, therefore, is to provide a device for in-situ measuring electrical properties of carbon nanotube array.

BRIEF DESCRIPTION OF THE DRAWINGS

Implementations of the present technology will now be described, by way of example only, with reference to the attached figures, wherein.

DETAILED DESCRIPTION

Figure 1:
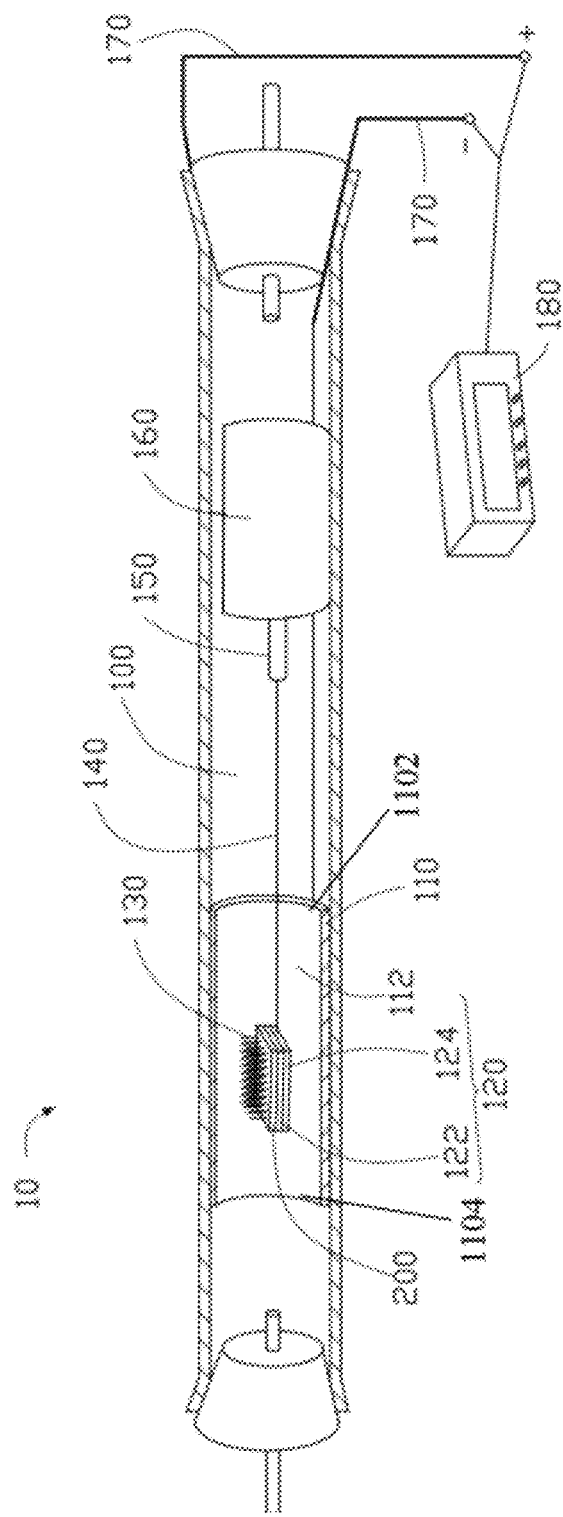
FIG. 1 is a schematic view of one embodiment of a device for in-situ measuring electrical properties of carbon nanotube array.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale, and the proportions of certain parts may be exaggerated to illustrate details and features better. The description is not to be considered as limiting the scope of the embodiments described herein.

Several definitions that apply throughout this disclosure will now be presented.

The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising" means "including, but not necessarily limited to"; it specifically indicates open-ended inclusion or membership in a so-described combination, group, series and the like.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Referring to FIG. 1, a device 10 for in-situ measuring electrical properties of a carbon nanotube array 130 comprises a chamber 100, a substrate 120, a first electrode 110, a connecting wire 140, a second electrode 150, a support structure 160, a measuring meter 180, and some conductive wires 170. The substrate 120, the first electrode 110, the connecting wire 140, the second electrode 150, and the support structure 160 are located inside of the chamber 100. The measuring meter 180 is located outside of the chamber 100. The measuring meter 180 is electrically connected to the first electrode 110 and the second electrode 150 by the conductive wires 170.

The material of the chamber 100 can be selected according to need. In one embodiment, the material of the chamber 100 is quartz. In one embodiment, the outside of the chamber 100 is surrounded by a shield layer (not shown). The shield layer is used to prevent the measurement of the electrical properties of the carbon nanotube array 130 from being interfered. The material of the shield layer can be nickel or electro-resistance alloy.

The substrate 120 comprises a support substrate 124 and a growth substrate 122. The growth substrate 122 can be located on a surface of the support substrate 124. The support substrate 124 is used to support the growth substrate 122 and make the growth substrate 122 suspend in the chamber 100. In one embodiment, the support substrate 124 is made of insulating material. The material of the support substrate 124 can be carbon material, silicon, or silica, so that the growth environment of the carbon nanotube array 130 in the chamber 100 would not be contaminated. In one embodiment, the material of the support substrate 124 is quartz.

The growth substrate 122 can be a carbon nanotube structure. The carbon nanotube structure can be used for growing carbon nanotubes. The carbon nanotube structure still can be a conductor at the growing temperature of the carbon nanotubes. The growth substrate 122 can be a drawn carbon nanotube film, a flocculated carbon nanotube film, or a pressed carbon nanotube film. In one embodiment, the growth substrate 122 is a flocculated carbon nanotube film.

Figure 2:
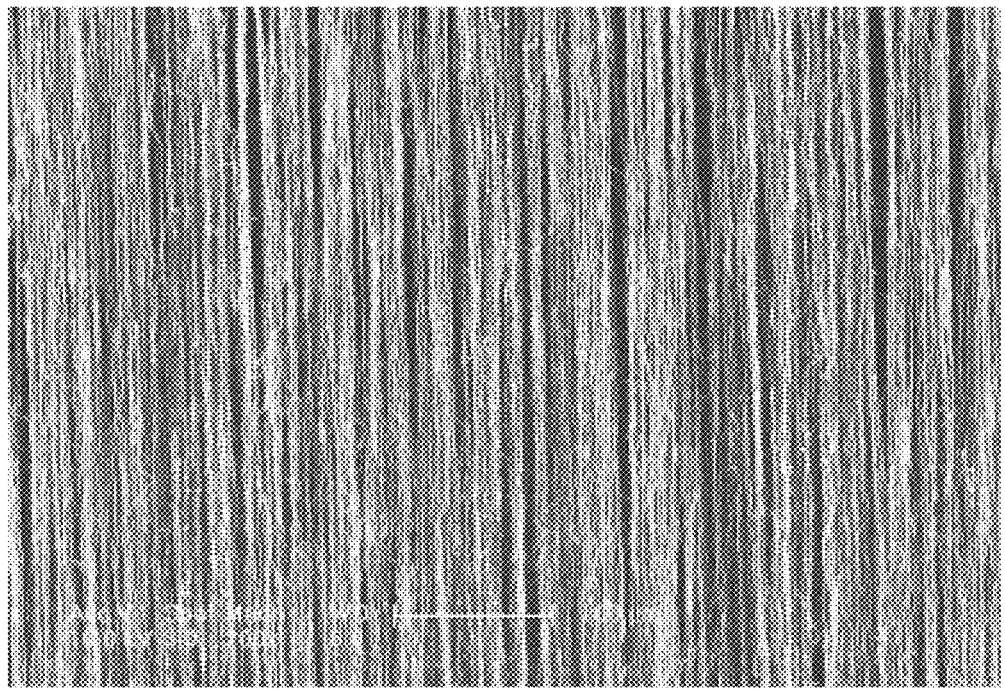
FIG. 2 is a scanning electron microscope (SEM) image of a drawn carbon nanotube film.

Referring to FIG. 2, the drawn carbon nanotube film comprises a plurality of successive and oriented carbon nanotubes joined end-to-end by van der Waals attractive force therebetween. The carbon nanotubes in the drawn carbon nanotube film extend along the same direction. The carbon nanotubes are parallel to a surface of the drawn carbon nanotube film. The drawn carbon nanotube film is a free-standing film. The drawn carbon nanotube film can bend to desired shapes without breaking.

If the growth substrate 122 comprises at least two stacked drawn carbon nanotube films, adjacent drawn carbon nanotube films can be combined by only the van der Waals attractive force therebetween. Additionally, when the carbon nanotubes in the drawn carbon nanotube film are aligned along one preferred orientation, an angle can exist between the orientations of carbon nanotubes in adjacent drawn carbon nanotube films, whether stacked or adjacent. An angle between the aligned directions of the carbon nanotubes in two adjacent drawn carbon nanotube films can be in a range from about 0 degrees to about 90 degrees.

Figure 3:
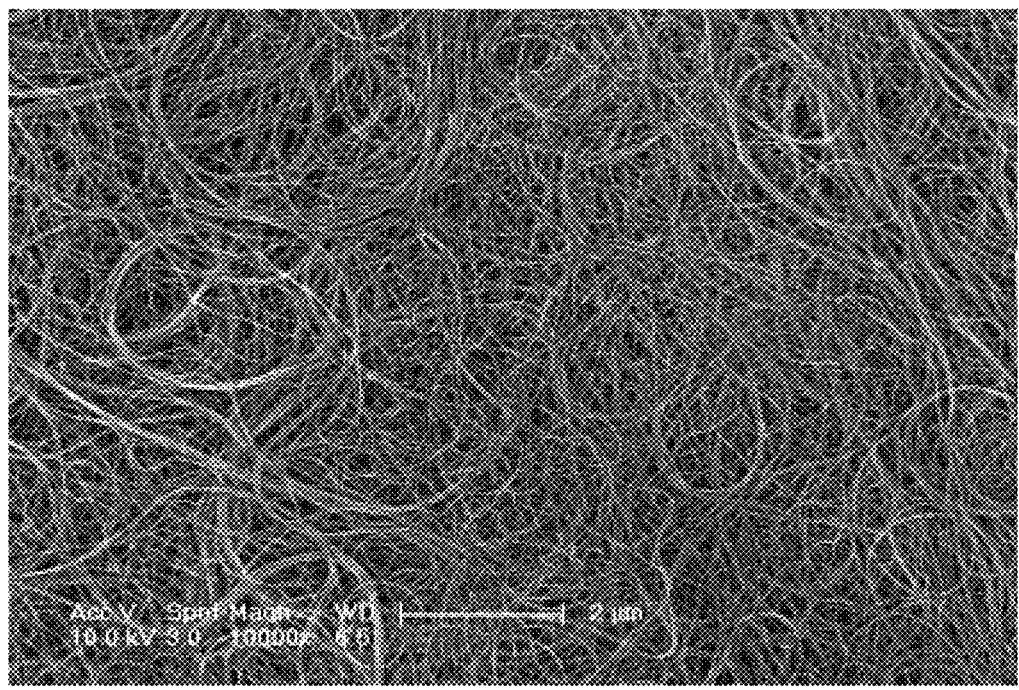
FIG. 3 is an SEM image of a flocculated carbon nanotube film.

Referring to FIG. 3, the flocculated carbon nanotube film comprises a plurality of long, curved, disordered carbon nanotubes entangled with each other. The flocculated carbon nanotube film can be isotropic. The carbon nanotubes can be substantially uniformly dispersed in the flocculated carbon nanotube film. Adjacent carbon nanotubes are acted upon by van der Waals attractive force to obtain an entangled structure. Due to the carbon nanotubes in the flocculated carbon nanotube film being entangled with each other, the flocculated carbon nanotube film has excellent durability and can be fashioned into desired shapes with a low risk to the integrity of the flocculated carbon nanotube film. Further, the flocculated carbon nanotube film is a free-standing film.

Figure 4:
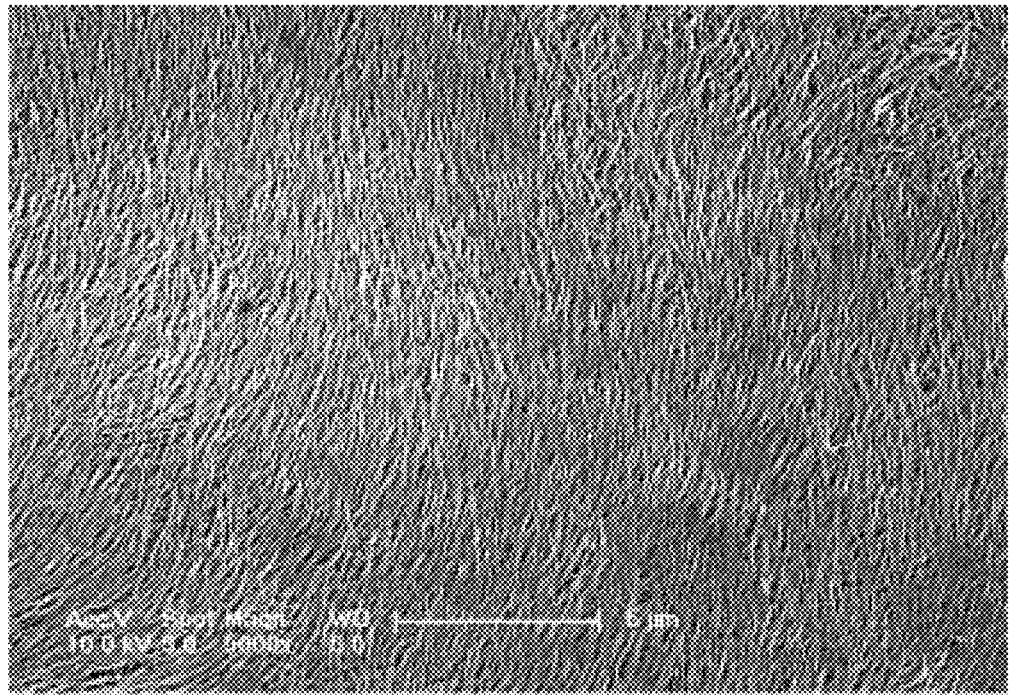
FIG. 4 is an SEM image of a pressed carbon nanotube film including a plurality of carbon nanotubes arranged along the same direction.
Figure 5:
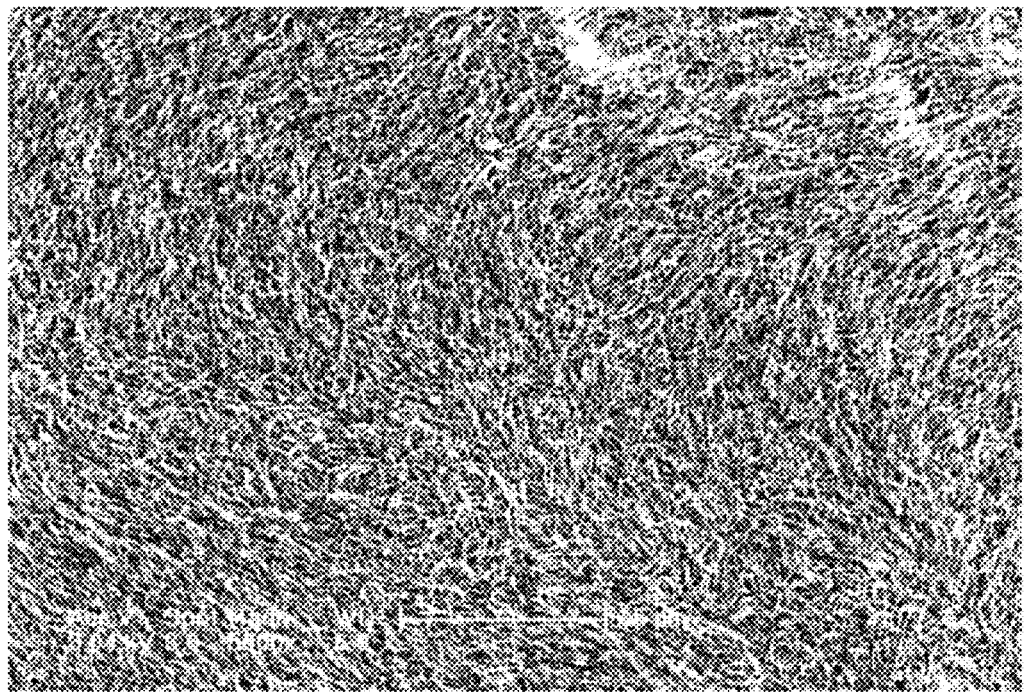
FIG. 5 is an SEM image of a pressed carbon nanotube film including a plurality of carbon nanotubes arranged along different directions.

Referring to FIGS. 4 and 5, the pressed carbon nanotube film comprises a plurality of carbon nanotubes. The carbon nanotubes in the pressed carbon nanotube film can be arranged along the same direction, as shown in FIG. 4. The carbon nanotubes in the pressed carbon nanotube film can be arranged along different directions, as shown in FIG. 5. The carbon nanotubes in the pressed carbon nanotube film can rest upon each other. An angle between a primary alignment direction of the carbon nanotubes and a surface of the pressed carbon nanotube film is about 0 degrees to approximately 15 degrees. The greater the pressure applied, the smaller the angle obtained. If the carbon nanotubes in the pressed carbon nanotube film are arranged along different directions, the pressed carbon nanotube film can have properties that are identical in all directions substantially parallel to the surface of the pressed carbon nanotube film. Adjacent carbon nanotubes are attracted to each other and are joined by van der Waals attractive force. Therefore, the pressed carbon nanotube film is easy to bend to desired shapes without breaking. Further, the pressed carbon nanotube film is a free-standing film.

The term "free-standing" comprises, but not limited to, the carbon nanotube layer structure that does not have to be supported by a substrate. For example, the free-standing carbon nanotube layer structure can sustain the weight of itself when it is hoisted by a portion thereof without any significant damage to its structural integrity. So, if the free-standing carbon nanotube layer structure is placed between two separate supporters, a portion of the free-standing carbon nanotube layer structure, not in contact with the two supporters, would be suspended between the two supporters and yet maintain film structural integrity.

Figure 6:
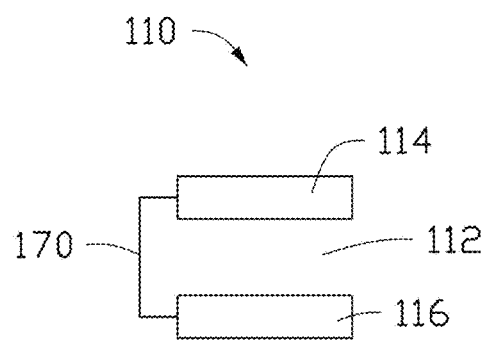
FIG. 6 is a schematic view of another embodiment of a first electrode of the device for in-situ measuring electrical properties of carbon nanotube array.

The first electrode 110 defines a cavity 112. The first electrode 110 has a first opening 1102 and a second opening 1104 opposite to the first opening 1102. In one embodiment, the first electrode 110 is a hollow cylinder, and the hollow portion of the cylinder forms the cavity 112, as shown in FIG. 1. In another embodiment, the first electrode 110 comprises a first conductive plate 114 and a second conductive plate 116 opposite to the first conductive plate 114, as shown in FIG. 6. The first conductive plate 114 and the second conductive plate 116 are spaced from each other. One end of the first conductive plate 114 is connected to one end of the second conductive plate 116 by the conductive wires 170. The materials of the first electrode 110 can be conductive materials that do not contaminate the growth environment of the carbon nanotube array 130 in the chamber 100. Thus, the materials of the first electrode 110 can be carbon material, such as graphite, carbon fiber, carbon nanotube, graphene, or combinations thereof. In one embodiment, the first electrode 110 is a hollow cylinder formed by graphite.

Figure 7:
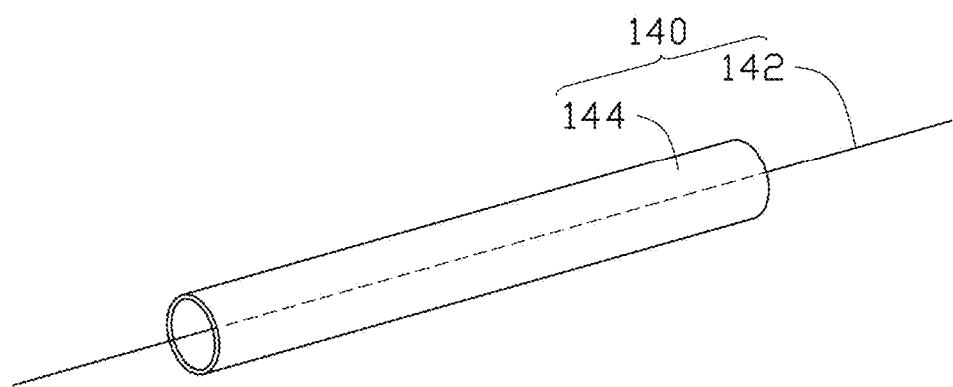
FIG. 7 is a schematic view of one embodiment of a connecting wire.

As shown in FIG. 7, the connecting wire 140 comprises a support element 144 and a conductive thread 142, and the support element 144 can be used to support the conductive thread 142. The conductive thread 142 can helically surround the outside surface of the support element 144. The conductive thread 142 can also be buried inside of the support element 144, and two opposite ends of the conductive thread 142 protrude out of the support element 144. The conductive thread 142 comprises a first thread end and a second thread end opposite to the first thread end. The first thread end of the conductive thread 142 is electrically connected to the second electrode 150, and the second thread end of the conductive thread 142 is electrically connected to the growth substrate 122. The material and the shape of the support element 144 are not limited. However, in order not to contaminate the growth environment of the carbon nanotube array 130 in the chamber 100, the material of the support element 144 can be carbon material. In one embodiment, the support element 144 is a quartz tube, the conductive thread 142 is located inside of the quartz tube, and two opposite ends of the conductive thread 142 protrude out of the support element 144, as shown in FIG. 7. In another embodiment, the support element 144 is a quartz tube, and the conductive thread 142 helically surrounds the outside surface of the quartz tube.

Figure 10:
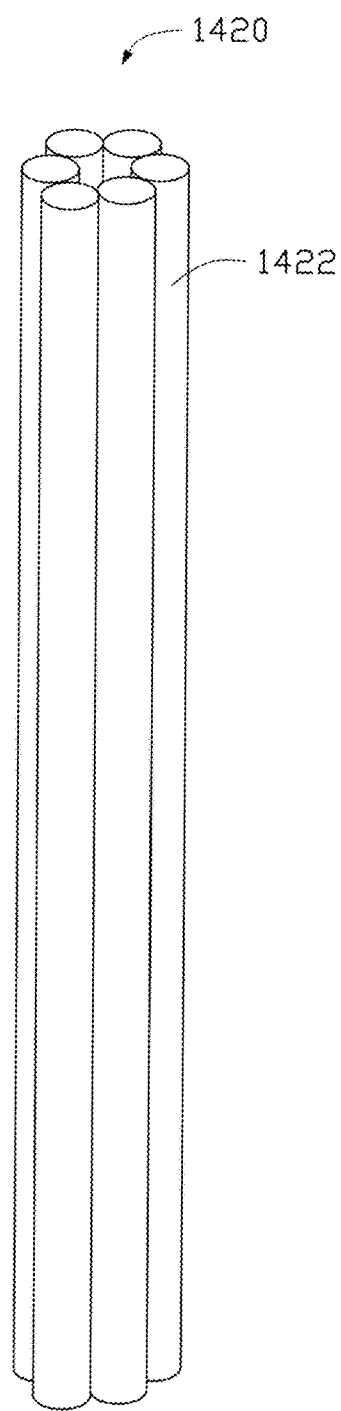
FIG. 10 is a schematic view of one embodiment of an untwisted carbon nanotube wire structure.
Figure 11:
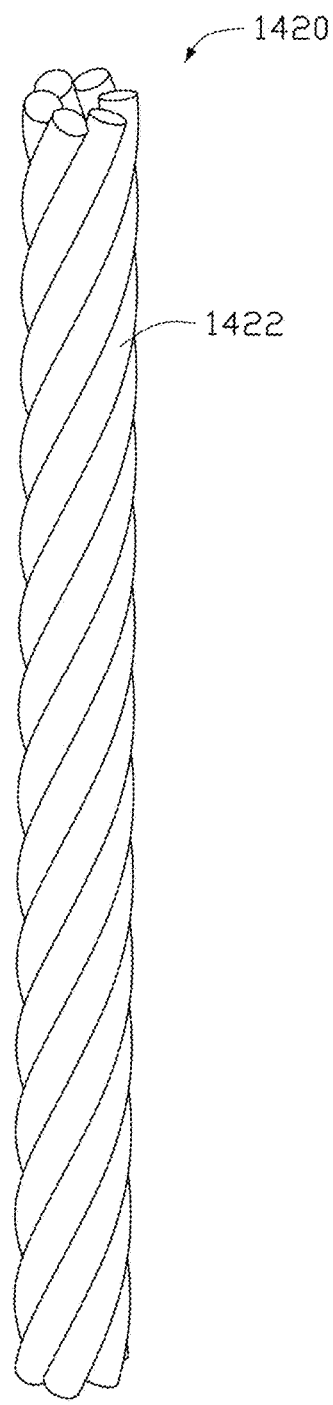
FIG. 11 is a schematic view of another embodiment of a twisted carbon nanotube wire structure.

The material of the conductive thread 142 is capable of withstanding the growth environment of the carbon nanotube array 130 and does not introduce impurities to contaminate the growth environment of the carbon nanotube array 130 in the chamber 100. Thus, the material of the conductive thread 142 can be carbon material. The conductive thread 142 can be a carbon nanotube wire structure 1420. Referring to FIG. 10, the carbon nanotube wire structure 1420 can comprise a plurality of carbon nanotube wires 1422 substantially parallel with each other. Referring to FIG. 11, the carbon nanotube wire structure 1420 can also comprise a plurality of carbon nanotube wires 1422 twisted with each other.

Figure 12:
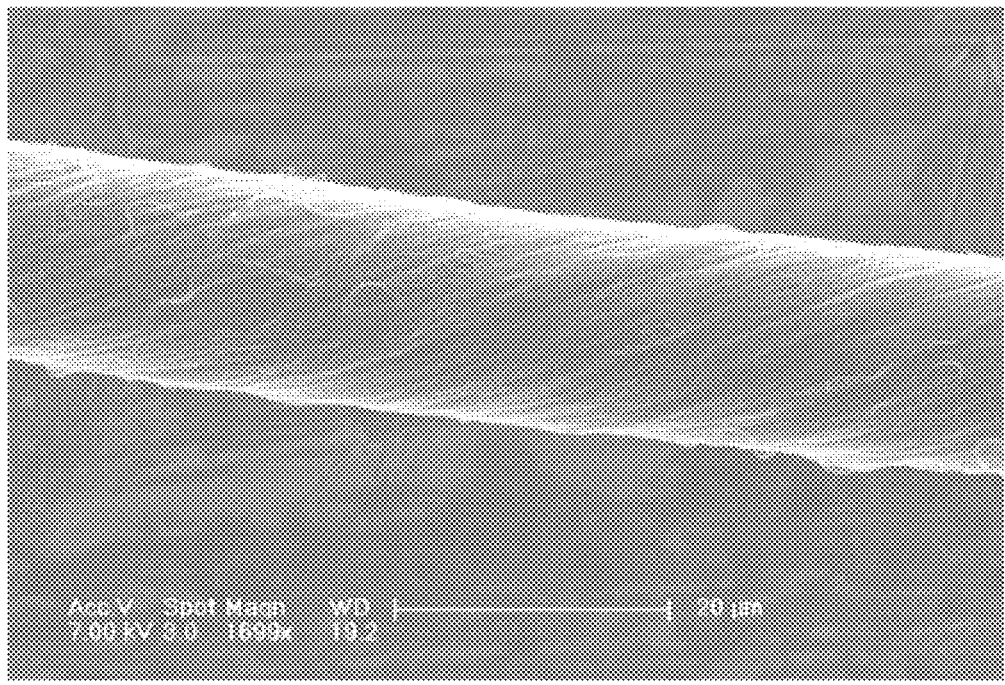
FIG. 12 is an SEM image of a twisted carbon nanotube wire.
Figure 13:
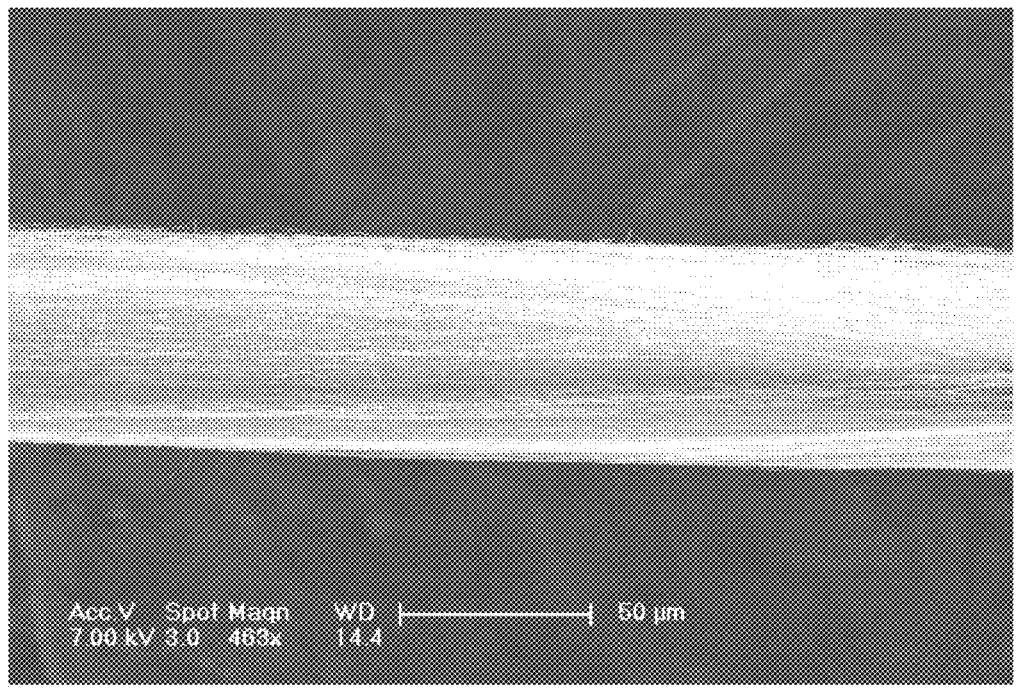
FIG. 13 is an SEM image of an untwisted carbon nanotube wire.

The carbon nanotube wire 1422 can be a twisted carbon nanotube wire or an untwisted carbon nanotube wire. Referring to FIG. 12, the twisted carbon nanotube wire 1422 comprises a plurality of carbon nanotubes helically oriented around an axial direction of the twisted carbon nanotube wire 1422. Referring to FIG. 13, the untwisted carbon nanotube wire 1422 comprises a plurality of carbon nanotubes substantially extending along a same direction (i.e., a direction along the length of the untwisted carbon nanotube wire 1422), and the carbon nanotubes are substantially parallel to the axis of the untwisted carbon nanotube wire 1422. More specifically, the untwisted carbon nanotube wire 1422 comprises a plurality of successive carbon nanotubes joined end to end by van der Waals attractive force therebetween.

A length of the carbon nanotube wire 1422 can be set as desired. A diameter of the carbon nanotube wire 1422 can be in a range from about 0.5 nanometers to about 100 micrometers. The carbon nanotubes in the carbon nanotube wire 1422 can be single-walled, double-walled, or multi-walled carbon nanotubes.

Figure 8:
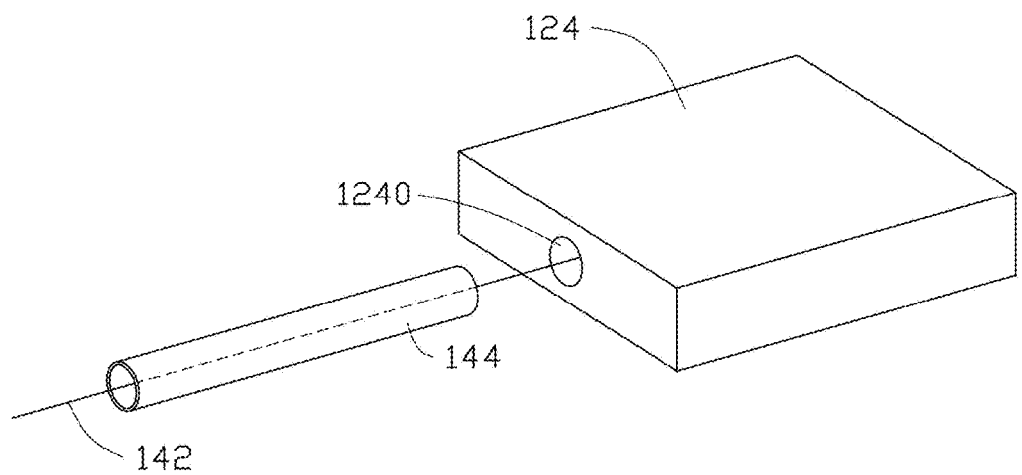
FIG. 8 is a three-dimensional exploded schematic view of one embodiment of a structure that is formed by the connecting wire and a support structure.

In addition to electrically connecting the growth substrate 122 and the second electrode 150, the connecting wire 140 can be used to make the growth substrate 122 suspend in the cavity 112 of the first electrode 110. The connecting wire 140 cooperates with the support substrate 124 so that the growth substrate 122 is suspended in the cavity 112 of the first electrode 110. Referring to FIG. 8, a hole 1240 is defined in the support substrate 124; the support element 144 comprises a first support end and a second support end opposite to the first support end, the first support end of the support element 144 is inserted into the hole 1240, and the second support end of the support element 144 is connected to the second electrode 150, so that the support substrate 124 is suspended in the cavity 112 by the support element 144. The second thread end of the conductive thread 142 is protruded out of the support element 144 and electrically connected to the growth substrate 122.

Figure 9:
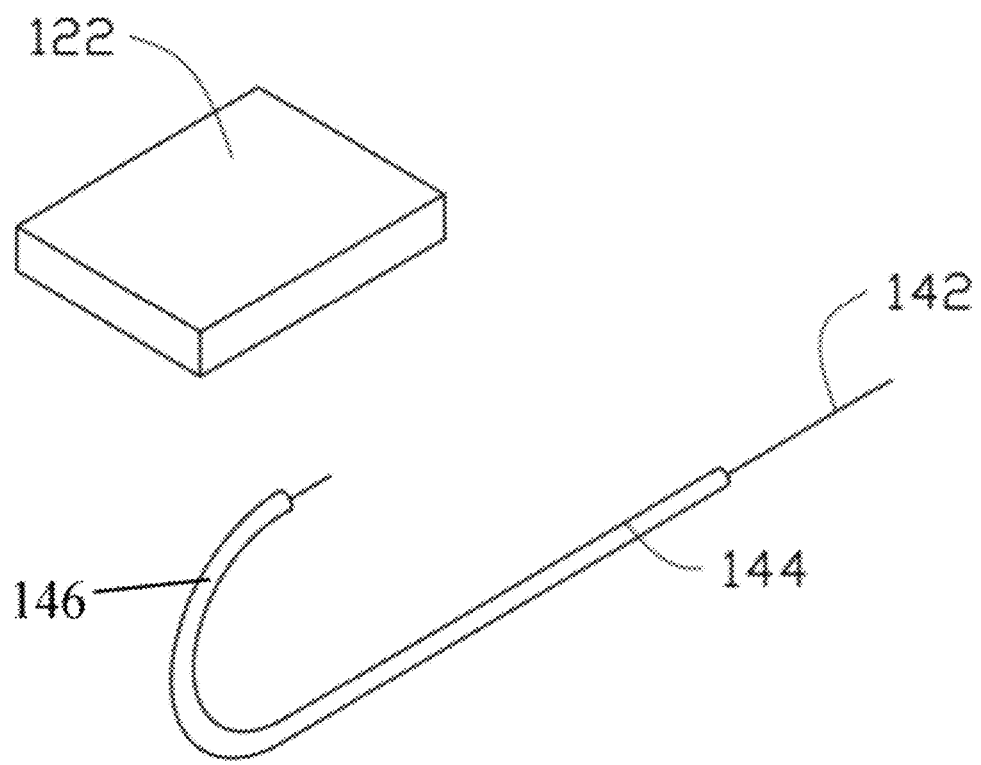
FIG. 9 is a three-dimensional exploded schematic view of another embodiment of the structure that is formed by the connecting wire and the support structure.

In one embodiment, as shown in FIG. 9, a portion of the support element 144 that is near the first electrode 110 can be bent to form an annular structure 146, and the support substrate 124 is located on the annular structure 146, so that the support substrate 124 is suspended in the cavity 112 of the first electrode 110. In one embodiment, the support element 144 is a quartz tube; a portion of the quartz tube near the first electrode 110 is bent to form the annular structure 146; and the growth substrate 122 being free-standing structure is in direct contact with the annular structure 146, and the support substrate 124 is omitted, as shown in FIG. 9.

Figure 14:
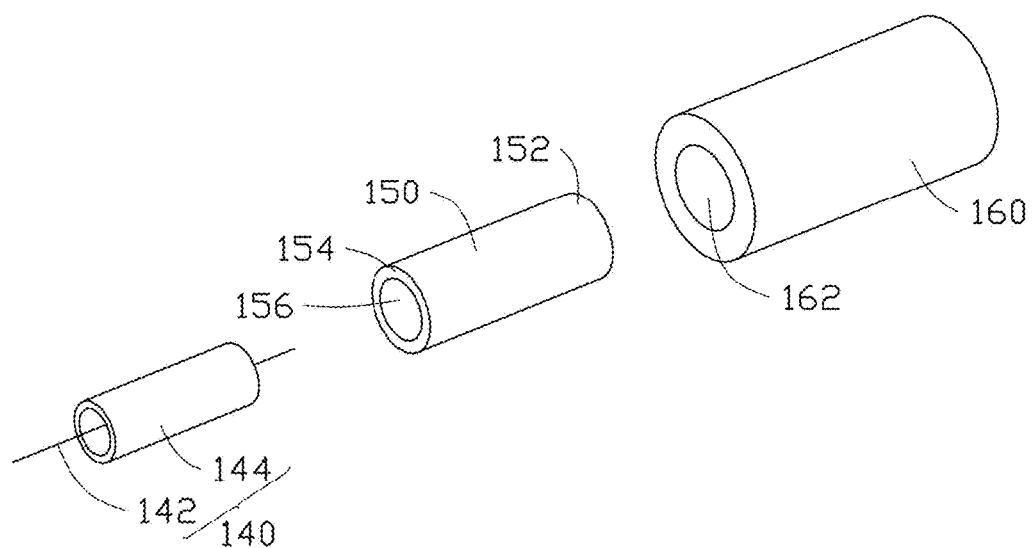
FIG. 14 is a three-dimensional exploded schematic view of one embodiment of a structure that is formed by the connecting wire, a second electrode, and the support structure.

As shown in FIG. 14, the second electrode 150 comprises a first end 152 and a second end 154 opposite to the first end 152. The second end 154 is used to fix the connecting wire 140, and the first end 152 is supported by the support structure 160. One end of the support structure 160 defines a second hole 162. The first end 152 of the second electrode 150 is inserted into the second hole 162 so that the second electrode 150 is suspended in the chamber 100. The second end 154 of the second electrode 150 defines a first hole 156, and one end of the connecting wire 140 is inserted into the first hole 156. In one embodiment, one end of the support element 144 is inserted into the first hole 156, so that the connecting wire 140 is suspended in the chamber 100, as shown in FIG. 14. The substrate 120 supported by the connecting wire 140 can be suspended in the cavity 112 of the first electrode 110, because the connecting wire 140 is suspended in the chamber 100. Accordingly, the growth substrate 122 supported by the support substrate 124 can also be suspended in the cavity 112 of the first electrode 110.

The material of the second electrode 150 can be a conductive material which does not contaminate the growth environment of the carbon nanotube array 130 in the chamber 100. Thus, the material of the second electrode 150 can be carbon material, such as graphite, carbon fiber, carbon nanotube, graphene, or combinations thereof. In one embodiment, the second electrode 150 is a cylinder formed by graphite. The shape and material of the support structure 160 can be selected according to need. In order not to contaminate the growth environment of the carbon nanotube array 130 in the chamber 100, the material of the support structure 160 can be carbon material, silicon, or silica. In one embodiment, the support structure 160 is a pillar made of quartz.

The measuring meter 180 has a first terminal and a second terminal opposite to the first terminal. The first terminal of the measuring meter 180 is electrically connected to the first electrode 110 by the conductive wires 170. The second terminal of the measuring meter 180 is electrically connected to the second electrode 150 by the conductive wires 170. The measuring meter 180 can be a voltmeter, an ammeter, a capacitive table, a resistance meter, an electrometer, or a multimeter. In one embodiment, the measuring meter 180 is an electrometer Keithley6517A. When the measuring meter 180 is a voltmeter, the open circuit voltage of the carbon nanotube array 130 can be obtained. When the measuring meter 180 is an ammeter, the short circuit current of the carbon nanotube array 130 can be obtained. When the measuring meter 180 is a capacitive table, the capacitance of the carbon nanotube array 130 can be obtained. When the measuring meter 180 is a multimeter or an electrometer Keithley6517A, the open circuit voltage, the short circuit current, or the equivalent resistance of the carbon nanotube array 130 can be obtained.

Because the conductive wires 170 are required to extend from outside into the chamber 100, in order not to contaminate the growth environment of the carbon nanotube array 130 in the chamber 100, the material of the conductive wires 170 can be the carbon nanotube wire structure 1420.

Furthermore, the device 10 comprises a heater (not shown in figures) which is used to heat the chamber 100, in particular, to directly heat the growth substrate 122.

In one embodiment, the use of the device 10 comprises follow steps:

S1, providing the growth substrate 122 having a first surface and a second surface opposite to the first surface on the substrate 120, wherein the second surface of the growth substrate 122 is in direct contact with the support substrate 124;

S2, providing a catalyst layer 200 on the first surface of the growth substrate 122 to form a composite structure;

S3, placing the composite structure in the chamber 100;

S4, supplying the carbon source gas, protective gas, and hydrogen to the chamber 100, and growing the carbon nanotube array 130 on the growth substrate 122 at a temperature from about 600 degrees Celsius to about 1200 degrees Celsius; and S5, obtaining the open circuit voltage, the short circuit current, or the equivalent resistance of the carbon nanotube array 130.

In the step S2, the catalyst layer 200 is made of a material selected from the group consisting of iron (Fe), cobalt (Co), nickel (Ni), and an alloy thereof. In one embodiment, the catalyst layer is Fe. The method for forming the catalyst layer 200 is not limited, such as lithography, sputtering, deposition, vapor deposition. In one embodiment, the catalyst layer 200 is vapor-deposited on the first surface of the growth substrate 122, and the thickness of the catalyst layer 200 is 1 nanometre. In one embodiment, the catalyst layer 200 is prepared by dripping about 1 mL mixed solution consisting of 50 mmol/L ethanol solution of $Fe(NO_3)_3$ and 50 mmol/L ethanol solution of $Al(NO_3)_3$ on the flocculated carbon nanotube film.

In the step S4, the carbon source gas comprises alkyne or hydrocarbon. The protective gas is an inert gas. In one embodiment, the protective gas is argon gas, and the volume flow of argon gas is 400 sccm. The temperature of the growth substrate is in a range from about 600 degrees Celsius to about 1200 degrees Celsius. In one embodiment, the chamber 100 is purged with argon gas, and then a mixed gas of $C_2H_2$ and hydrogen is supplied into the chamber 100, and the carbon nanotube array 130 is grown at about 700 degrees Celsius. The volume flow of $C_2H_2$ is in a range from about 1 sccm to about 1.5 sccm. The volume flow of hydrogen is about 200 sccm.

In the step S5, after obtaining the carbon nanotube array 130, the quantity of electric charge of the carbon nanotube array 130 can be obtained by formula: Q=U×C; wherein the quantity of electric charge is defined as Q, the voltage is defined as U, and the capacitance is defined as C.

Figure 15:
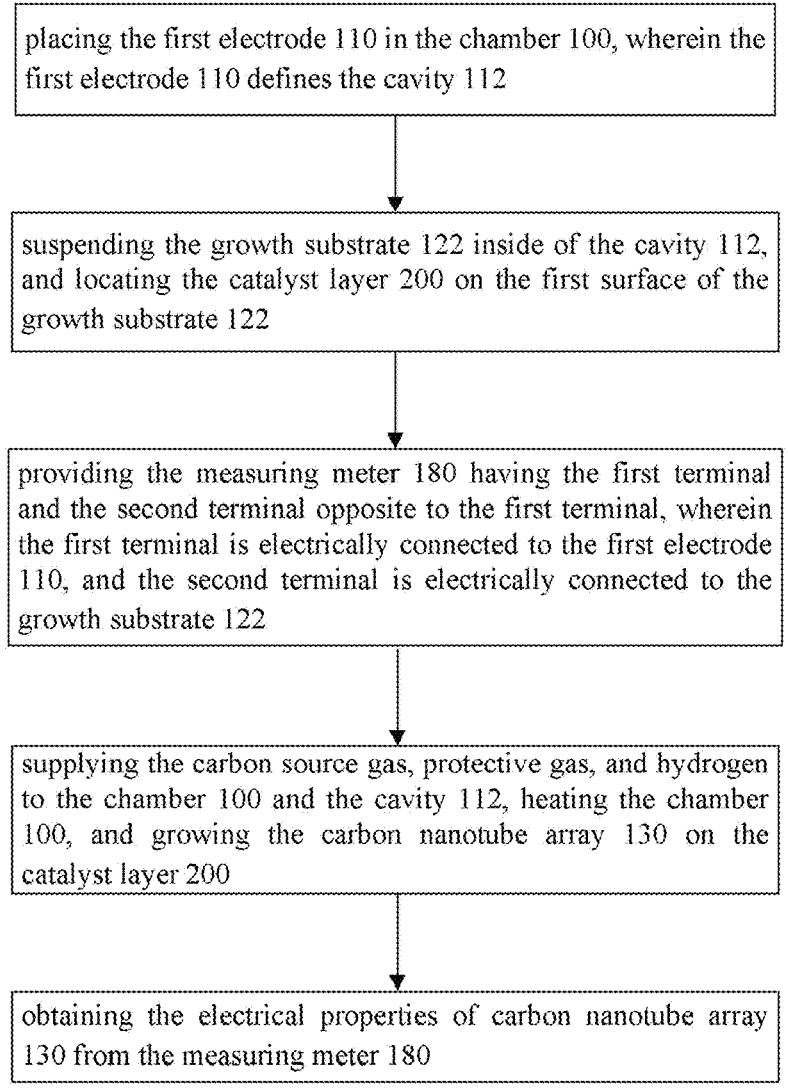
FIG. 15 is a process flow of one embodiment of a method for in-situ measuring electrical properties of carbon nanotube array.

Referring to FIGS. 1 and 15, in one embodiment, a method for in-situ measuring electrical properties of carbon nanotubes comprises the steps:

S1', placing the first electrode 110 in the chamber 100, wherein the first electrode 110 defines the cavity 112;

S2', suspending the growth substrate 122 inside of the cavity 112, and locating the catalyst layer 200 on the first surface of the growth substrate 122;

S3', providing the measuring meter 180 having the first terminal and the second terminal opposite to the first terminal, wherein the first terminal is electrically connected to the first electrode 110, and the second terminal is electrically connected to the growth substrate 122;

S4', supplying the carbon source gas, protective gas, and hydrogen to the chamber 100 and the cavity 112, heating the chamber 100, and growing the carbon nanotubes on the catalyst layer 200;

S5, obtaining the electrical properties of carbon nanotubes from the measuring meter 180.

In the step S1', the first electrode 110 needs to satisfy at least two conditions. The first condition is that the first electrode 110 is used for allowing the growth substrate 122 to be in an equipotential environment, to collect all electric charges generated during the growth of the carbon nanotubes. The second condition is that the first electrode 110 is used for allowing the gas flows of the carbon source gas and the protecting gas to pass. Thus, the first electrode 110 defines the cavity 112. When the growth substrate 122 is located inside of the cavity 112, the growth substrate 122 is located in the equipotential environment. In addition, the first electrode 110 has the first opening 1102 and the second opening 1104, so that the gas flows of the carbon source gas and the protecting gas pass through the cavity 112.

In one embodiment, the first electrode 110 is a hollow cylinder, and the hollow portion of the cylinder forms the cavity 112, as shown in FIG. 1. In another embodiment, the first electrode 110 comprises the first conductive plate 114 and the second conductive plate 116 opposite to the first conductive plate 114, the first conductive plate 114 and the second conductive plate 116 form the cavity 112, as shown in FIG. 6. The first conductive plate 114 and the second conductive plate 116 are spaced from each other. One end of the first conductive plate 114 is connected to one end of the second conductive plate 116 by the conductive wires 170. The materials of the first electrode 110 can be conductive materials that do not contaminate the growth environment of the carbon nanotubes in the chamber 100. Thus, the materials of the first electrode 110 can be carbon material, such as graphite, carbon fiber, carbon nanotube, graphene, or combinations thereof. In one embodiment, the first electrode 110 is a hollow cylinder formed by graphite In the step S2', the growth substrate 122 needs to satisfy at least two conditions. The first condition is that the growth substrate 122 can be used for growing carbon nanotubes. The second condition is that the growth substrate 122 can still be a conductor at the growing temperature of the carbon nanotubes. The growth substrate 122 can be a drawn carbon nanotube film, a flocculated carbon nanotube film, or a pressed carbon nanotube film. In one embodiment, the growth substrate 122 is a flocculated carbon nanotube film.

The growth substrate 122 needs to be suspended inside of the cavity 112 and spaced from the first electrode 110, and the growth substrate 122 cannot be in contact with the first electrode 110. The reason are as follows. The growth substrate 122 is suspended inside of the cavity 112. The first terminal of the measuring meter 180 is electrically connected to the first electrode 110, and the second terminal of the measuring meter 180 is electrically connected to the growth substrate 122. The carbon source gas and the hydrogen gas inside of the cavity 112 would be ionized into positive ions and negative ions, such as $H^+$ or $C_2H^-$ at the growing temperature of the carbon nanotubes. The electric charges are generated during the growth process of the carbon nanotubes of the carbon nanotube array 130. The electric charges are transferred to the positive ions and the negative ions. Thus, the positive ions and the negative ions are conductive and diffuse inside of the cavity 112. Thus, the conductive positive ions and the conductive negative ions would cause the growth substrate 122 to be electrically connected to the first electrode 110. The first electrode 110 collects the charged positive ions and the charged negative ions. However, the concentration of the positive ions and the negative ions are low, thus the equivalent resistances of the positive ions and the negative ions are large. The equivalent resistances of the positive ions and the negative ions are greater than the resistance of the support structure 160 at the temperature of growing the carbon nanotubes. When the support structure 160 is placed in the cavity 112 of the first electrode 110 and the material of the support structure 160 is quartz, the growth temperature of the carbon nanotubes will cause the quartz support structure 160 to be conductive. The support structure 160 is placed in a region away from the first electrode 110, to prevent the support structure 160 from being electrically conductive. Thus, the current measured by the measuring meter 180 is the current transferred by the positive ions and the negative ions. The current measured by the measuring meter 180 is the current generated during the growth of the carbon nanotubes. A loop is formed between the measuring meter 180, the first electrode 110, the positive ions or negative ions, the growth substrate 122, and the carbon nanotubes. Thus, the electrical properties of carbon nanotubes can be measured by the measuring meter 180.

The principle of in-situ measuring electrical properties of carbon nanotubes is as follow. The electric charges that is generated in growing the carbon nanotubes is transferred to the positive ions and the negative ions that are generated by the ionization of the carbon source gas and the hydrogen. When the growth substrate 122 is suspend in the cavity 112, the first electrode 110 collects the charged positive ions and the charged negative ions. The electric charges carried by the positive ions and the negative ions can pass through the measuring meter 180. Therefore, the current measured by the measuring meter 180 is the current generated during the growth of the carbon nanotubes. The electric charges generated in growing the carbon nanotubes and the electric charges transferring can be obtained.

If the growth substrate 122 directly contacts with the first electrode 110, the charges of the carbon nanotubes would be transported to the first electrode 110 by the growth substrate 122 due to the good conductivity of the growth substrate 122. If the growth substrate 122 directly contacts with the first electrode 110, the electric charges collected by the first electrode 110 cannot pass through the measuring meter 180. Thus, the electrical properties of carbon nanotubes cannot be measured by the measuring meter 180. The electric charges generation and transferring in growing the carbo nanotubes cannot be obtained. Thus, it is necessary to suspend the growth substrate 122 in the cavity 112 of the first electrode 110.

The method for suspending the growth substrate 122 inside of the cavity 112 is not limited. In one embodiment, one method for suspending the growth substrate 122 inside of the cavity 112 is provided. The method is described below.

The connecting wire 140, the second electrode 150, and the support structure 160 are inside of the chamber 100. The connecting wire 140 comprises the support element 144 and the conductive thread 142, and the support element 144 can be used to support the conductive thread 142. The first thread end of the conductive thread 142 is electrically connected to the second electrode 150, and the second thread end of the conductive thread 142 is electrically connected to the growth substrate 122. The conductive thread 142 can helically surround the outside surface of the support element 144. The conductive thread 142 can also be buried inside of the support element 144, and two opposite ends of the conductive thread 142 protrude out of the support element 144. The support structure 160 defines the second hole 162. The second electrode 150 comprises the first end 152 and the second end 154 opposite to the first end 152. The first end 152 of the second electrode 150 is inserted into the second hole 162 so that the second electrode 150 is suspended in the chamber 100. The second end 154 of the second electrode 150 defines the first hole 156, and one end of the support element 144 is inserted into the first hole 156 so that the connecting wire 140 is suspended in the chamber 100, as shown in FIG. 14.

A portion of the support element 144 near the first electrode 110 is bent to form the annular structure 146. The growth substrate 122 is a free-standing structure. Thus, the support substrate 124 is optional, and the growth substrate 122 is in contact with the annular structure 146, as shown in FIG. 9. The materials of the connecting wire 140, the second electrode 150, the support structure 160, and the method for disposing the catalyst layer 200 are described in detail above, and will not be described again.

In the step S3', in one embodiment, the first thread end of the conductive thread 142 is electrically connected to the second electrode 150, and the second thread end of the conductive thread 142 is electrically connected to the growth substrate 122. Thus, the measuring meter 180 is electrically connected to the growth substrate 122 by electrically connecting the second terminal of the measuring meter 180 to the second electrode 150.

In the step S4', the method for growing the carbon nanotubes is not limited. In one embodiment, the carbon source gas, the protective gas, and the hydrogen are supplied to the chamber 100, and the chamber 100 is heated to be the temperature from about 600 degrees Celsius to about 1200 degrees Celsius, to grow the carbon nanotubes on the catalyst layer 200. The specific parameters of the carbon source gas, the protecting gas and the hydrogen gas, and the heating modes are described in detail above, and are not repeated here.

In the step S5', the measuring meter 180 can be a voltmeter, an ammeter, a capacitive table, a resistance meter, an electrometer, or a multimeter. The electrical properties of carbon nanotubes can be read from the measuring meter 180. The electrical properties of the carbon nanotubes reflect the charge generation and the charge transfer in the growth of carbon nanotubes. In one embodiment, the measuring meter 180 is an electrometer Keithley6517A. When the measuring meter 180 is a voltmeter, the open circuit voltage of the carbon nanotubes can be obtained. When the measuring meter 180 is an ammeter, the short circuit current of the carbon nanotubes can be obtained. When the measuring meter 180 is a capacitive table, the capacitance of the carbon nanotubes can be obtained. When the measuring meter 180 is a multimeter or the electrometer Keithley6517A, the open circuit voltage, the short circuit current, or the equivalent resistance of the carbon nanotubes can be obtained. In addition, the quantity of electric charge of the carbon nanotubes can be obtained by the formula: $Q=U\times C$, wherein the quantity of electric charge is defined as Q, the voltage is defined as U, and the capacitance is defined as C.

Figure 16:
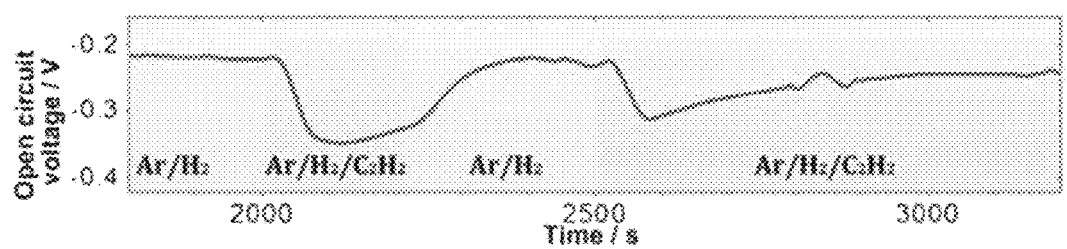
FIG. 16 is a curve of time-open circuit voltage measured by the device of FIG. 1 and the method of FIG. 15.

Referring to FIG. 16, the abscissa is the time, the ordinate is the open circuit voltage. When the flow of the carbon source gas $C_2H_2$ increases, the open circuit voltage becomes larger. When the flow of the carbon source gas $C_2H_2$ decreases, the open circuit voltage becomes smaller.

In the first time period from 0 to about 2000 seconds, only Ar and $H_2$ exist in the chamber 100, and there is no $C_2H_2$ in the chamber 100. The open circuit voltage is about −0.22 volts in the first time period. In the second time period from about 2000 seconds to about 2220 seconds, $C_2H_2$ are supplied into the chamber 100, and there are simultaneously Ar, $H_2$, and $C_2H_2$ in the chamber 100. The open circuit voltage is gradually increased, and the maximum of the open circuit voltage is about −0.35 volts in the second time period.

Subsequently, when the flow of the carbon source gas $C_2H_2$ decreases, the open circuit voltage becomes smaller again. In the third time period from about 2220 seconds to about 2500 seconds, there is no $C_2H_2$ in the chamber 100, and only Ar and $H_2$ are in the chamber 100. The open circuit voltage is gradually reduced to about −0.22 volts. And then $C_2H_2$ is supplied into the chamber 100, the open circuit voltage gradually increases.

As shown in FIG. 16, the flow of the carbon source gas in the chamber 100 can affect the value of the open circuit voltage. The carbon nanotube array 130 is actually grown during introducing the carbon source gas. Therefore, the carbon nanotubes of the carbon nanotube array 130 can affect the value of the open circuit voltage. It can be inferred that the voltage obtained from the measuring meter 180 can reflect the open circuit voltage of the carbon nanotube array 130.

Figure 17:
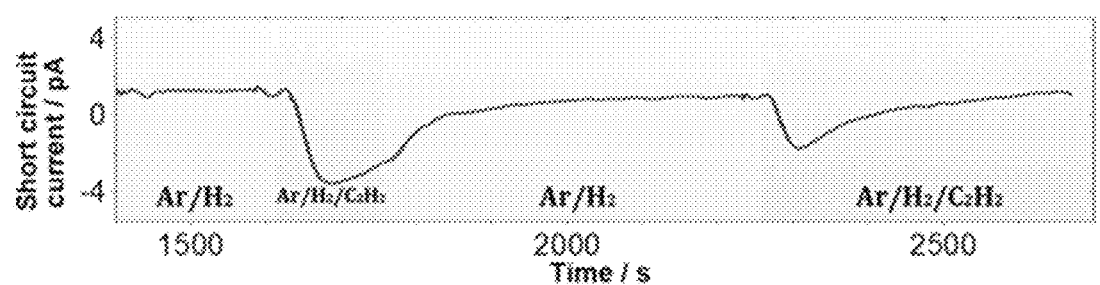
FIG. 17 is a curve of time-short circuit current measured by the device of FIG. 1 and the method of FIG. 15.

Referring to FIG. 17, the abscissa is the time, the ordinate is the short circuit current. When the flow of the carbon source gas $C_2H_2$ increases, the short-circuit current becomes larger. When the flow of the carbon source gas $C_2H_2$ decreases, the short-circuit current becomes smaller.

In the first time period from 0 to about 1600 seconds, only Ar and $H_2$ exist in the chamber 100, and there is no $C_2H_2$ in the chamber 100. The short circuit current is almost about 0 pA in the first time period. In the second time period from about 1600 seconds to about 1750 seconds, $C_2H_2$ are supplied into the chamber 100, and there are simultaneously Ar, $H_2$, and $C_2H_2$ in the chamber 100. The short circuit current begins to appear and gradually increases, and the maximum of the short circuit current is about −4 pA in the second time period. Subsequently, when the flow of the carbon source gas $C_2H_2$ decreases, the short-circuit current becomes smaller again. In the third time period from about 1750 seconds to about 2250 seconds, there is no $C_2H_2$ in the chamber 100, and only Ar and $H_2$ are in the chamber 100. The short circuit current is gradually reduced to 0 pA. And then $C_2H_2$ is supplied into the chamber 100, the short circuit current gradually increases.

As shown in FIG. 17, the flow of the carbon source gas in the chamber 100 can affect the value of the short circuit current. The carbon nanotube array 130 is actually grown during the carbon source gas is being introduced. Therefore, the carbon nanotubes of the carbon nanotube array 130 can affect the value of the short circuit current. It can be inferred that the current obtained from the measuring meter 180 can reflect the short circuit current of the carbon nanotube array 130.

From the analysis of FIGS. 16 and 17, it can be seen that the device 10 can detect the in-situ charge accumulation of the carbon nanotube array 130 at each time during the growth of the carbon nanotube array 130. Thus, the growth situation of carbon nanotubes can be obtained, which is great significance to study the growth mechanism of carbon nanotubes.

In summary, the carbon nanotube array 130 is always in the chamber 100 during the measurement of electrical properties of the carbon nanotube array 130, so that the carbon nanotube array 130 is always in the growth environment. The growth environment of the carbon nanotube array 130 is the same as the measurement environment of electrical properties of the carbon nanotube array 130. Therefore, the most intrinsic electrical properties of the carbon nanotube array 130 can be measured, which improves the accuracy of electrical properties of the carbon nanotube array 130.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in matters of shape, size and arrangement of the parts within the principles of the present disclosure up to, and including, the full extent established by the broad general meaning of the terms used in the claims.

Additionally, it is also to be understood that the above description and the claims drawn to a method may comprise some indication in reference to certain steps. However, the indication used is only to be viewed for identification purposes and not as a suggestion as to an order for the steps.

What is claimed is:

1. A device for in-situ measuring electrical properties of a carbon nanotube array, comprising:
a chamber, a substrate, a first electrode, a connecting wire, a second electrode, a support structure, and a measuring meter;
wherein the substrate, the first electrode, the connecting wire, the second electrode, and the support structure are located inside of the chamber; the measuring meter is located outside of the chamber, and the measuring meter is electrically connected to the first electrode and the second electrode; and the first electrode defines a cavity, and the substrate is suspended in the cavity and electrically connected to the second electrode.

2. The device of claim 1, wherein the second electrode comprises a first end and a second end opposite to the first end, and the second end defines a first hole; a part of the connecting wire is inserted into the first hole; and the support structure defines a second hole, and the first end is inserted into the second hole.

3. The device of claim 1, wherein the substrate comprises a growth substrate used for growing the carbon nanotube array, and the growth substrate is conductive at a growing temperature of the carbon nanotube array.

4. The device of claim 3, wherein the substrate further comprises a support substrate used to support the growth substrate.

5. The device of claim 3, wherein the growth substrate comprises a plurality of carbon nanotubes.

6. The device of claim 5, wherein the plurality of carbon nanotubes are entangled with each other.

7. The device of claim 3, wherein the connecting wire comprises a support element and a conductive thread, the support element is used to support the conductive thread; the conductive thread comprises a first thread end and a second thread end opposite to the first thread end, the first thread end is electrically connected to the second electrode, and the second thread end is electrically connected to the growth substrate.

8. The device of claim 7, wherein the conductive thread helically surrounds an outside surface of the support element.

9. The device of claim 7, wherein the conductive thread is buried inside of the support element, and two opposite ends of the conductive thread protrude out of the support element.

10. The device of claim 7, wherein the support element is a quartz tube.

11. The device of claim 7, wherein the conductive thread is a carbon nanotube wire structure comprising a plurality of carbon nanotubes joined end to end by van der Waals attractive force.

12. The device of claim 11, wherein the plurality of carbon nanotubes are helically oriented around an axial direction of the carbon nanotube wire structure.

13. The device of claim 11, wherein the plurality of carbon nanotubes substantially extends along the same direction.

14. The device of claim 1, wherein the first electrode is a hollow cylinder.

15. The device of claim 1, wherein the first electrode comprises a first conductive plate and a second conductive plate, wherein the first conductive plate is spaced from and electrically connected to the second conductive plate.

16. The device of claim 1, wherein the second electrode comprises a material that is selected from the group consisting of graphite, carbon fiber, carbon nanotube, and graphene.

\* \* \* \* \*